(12) United States Patent
Merianos et al.

(10) Patent No.: US 7,115,641 B2
(45) Date of Patent: Oct. 3, 2006

(54) ANTIMICROBIAL OXAZOLIDINE/IODOPROPYNYL-BUTYL CARBAMATE COMPOSITION CONTAINING LESS THAN 0.1WT% FREE FORMALDEHYDE

(75) Inventors: John J. Merianos, Middletown, NJ (US); Paul Garelick, South Plainfield, NJ (US); Susan Lindstrom, Ramsey, NJ (US); Xianbin Liu, Basking Ridge, NJ (US); Karen Winkowski, Sayreville, NJ (US)

(73) Assignee: ISP Investments Inc., Wilmington, DE (US)

( * ) Notice: Subject to any disclaimer, the term of this patent is extended or adjusted under 35 U.S.C. 154(b) by 304 days.

(21) Appl. No.: 10/770,280

(22) Filed: Feb. 2, 2004

(65) Prior Publication Data

US 2004/0157899 A1   Aug. 12, 2004

Related U.S. Application Data

(63) Continuation-in-part of application No. 10/357,881, filed on Feb. 4, 2003, now abandoned.

(51) Int. Cl.
*A01N 43/76* (2006.01)
*A01N 47/12* (2006.01)
*A61L 2/16* (2006.01)

(52) U.S. Cl. ...................... 514/375; 514/479; 514/769; 514/772; 514/772.4; 514/789

(58) Field of Classification Search ........ 514/374–377, 514/479, 769, 789, 772.4
See application file for complete search history.

(56) References Cited

FOREIGN PATENT DOCUMENTS

GB        2354771        *    4/2001

* cited by examiner

*Primary Examiner*—John Pak
(74) *Attorney, Agent, or Firm*—Walter Katz

(57) ABSTRACT

This invention relates to a broad spectrum antimicrobial composition, effective against gram negative and gram positive bacteria and fungi, which comprises a synergistic composition comprising iodopropynyl butyl carbamate and a bicyclic hydroxymethyl oxazolidine containing less than 0.1% of free formaldehyde.

11 Claims, No Drawings

ANTIMICROBIAL OXAZOLIDINE/IODOPROPYNYL-BUTYL CARBAMATE COMPOSITION CONTAINING LESS THAN 0.1WT% FREE FORMALDEHYDE

CROSS REFERENCE TO RELATED PATENT APPLICATION

This application is a continuation-in-part of U.S. patent application Ser. No. 10/357,881, filed on Feb. 4, 2003 (abandoned).

FIELD OF THE INVENTION

The invention is primarily directed to a synergistic composition containing oxazolidine having low free formaldehyde and iodopropynyl butyl carbamate (IPBC) in a liquid glycol, water or phenoxy ethanol medium and to the preparation of the composition which is useful as a preservative in cosmetic, personal care and industrial formulations.

BACKGROUND OF THE INVENTION

Bicyclic oxazolidines are generally known and used as hardeners, corrosion inhibitors, lubricants, adhesive additives, enamel coatings and curing agents as described in U.S. Pat. Nos. 4,064,055, 4,277,353, 4,277,354, 3,982,993, 3,888,625, 3,802,897, 3,773,730, 3,725,350, 3,738,992, 3,706,950, 5,187,019, 5,684,114, 3,802,897, 3,705,832, 3,695,326, 3,281,311, 3,256,137, 3,281,310 and 3,297,611. Mixtures of bicyclic oxazolidine, used as a preservative in latex paints and emulsions, pigmented dispersions, slurries, adhesives, caulks, sealants and metal working fluids to prevent bacterial decomposition have been described in ISP BIOTREND bulletin 0040-R6, dated March 2002 One such mixture is marked under the trademark NUOSEPT 95. Also, a limited group of monocyclic oxazolidines disclosed in U.S. Pat. Nos. 4,841,064, 4,855,312 and Canadian patents 1,221,096 and 1,252,041 are defined as having biocidal properties.

Additionally, the preparation of the bicyclic compounds is set forth in technical bulletins TB 15 and TDS 40 issued by ANGUS Chemical Company and involves the condensation reaction between equimolar amounts of paraformaldehyde and an aminoalcohol. One of the challenges facing oxazolidine manufacturers and formulators using this product is the presence of free formaldehyde which has been found objectionable from human safety and environmental considerations. The stringent limits of formaldehyde in human exposure and air emissions imposed by foreign and domestic agencies, such as the Occupational Safety and Health Administration and the Environmental Protection Agency, require costly purification in the manufacture and use of formaldehyde derived oxazolidines. Additionally, in the manufacture of biheterocyclic compounds such as oxymethylene oxazolidine, it is desirable to minimize or eliminate the formation of alkoxylated derivatives which significantly reduce its activity and stability.

IPBC has been independently described as a biocide for certain algae in U.S. Pat. No. 6,121,198. However, this carbamate exhibits mostly antifungal efficacy against several other species.

Accordingly, it is an object of this invention to provide a broad spectrum antimicrobial liquid composition which has less than 0.1 wt. % of free formaldehyde.

Another object is to provide a liquid biocidal oxazolidine composition which is non-toxic to humans and safe for incorporation in topical personal care formulations.

Another object of the invention is to provide a commercially feasible and economical process for producing a bicyclic oxazolidine and IPBC mixture containing low levels of free formaldehyde.

Still another object is to prepare a synergistic mixture of biocides which is effective against gram negative and gram positive bacteria as well as fungi.

Still another object is to provide a clear liquid composition containing a mixture of oxazolidine and IPBC which is resistant to precipitation or crystallization and which is substantially colorless.

These and other objects and advantages of the invention will become apparent from the following description and disclosure.

SUMMARY OF THE INVENTION

In accordance with the present invention, there is provided (a) a clear aqueous glycol solution of a synergistic antimicrobial hydroxymethyl bicyclic oxazolidine (HMBO)/IPBC composition which contains less than 0.1 wt. % of free formaldehyde and other functional group substitutions and (b) a process for making the composition which requires reacting a glycol slurry of paraformaldehyde with a controlled critical molar amount of tris(hydroxymethyl)-aminomethane before addition of a predetermined amount of IPBC.

DETAILED DESCRIPTION OF THE INVENTION

The present invention is directed to a synergistic, biocidal composition that is non-toxic to humans and the environment under normal conditions of exposure and is suitable for controlling harmful bacteria and fungi which comprises a 1.0–60 wt. % glycol solution containing, as the active components, a mixture of between 20 and 60 wt. % of said aliphatic, hydroxymethyl bicyclic oxazolidine (HMBO), particularly the bicyclic hydroxymethyl oxazolidine, and between 0.01 and 10 wt. % IPBC. In the composition, bicyclic hydroxymethyl oxazolidine is preferred and optionally may contain up to 5 wt. % of another aliphatic oxazolidine biocide as in a blend or admixture. However, synergistic biocidal properties between hydroxymethyl oxazolidine and IPBC have been discovered.

This synergistic composition is prepared by a process which demands observance of certain critical parameters. More specifically, for the preparation of the bicyclic hydroxymethyl oxazolidine (HMBO)/IPBC composition, paraformaldehyde as a uniform slurry in a glycol reaction medium is reacted with a critical 0.75–5.3% molar excess, preferably a 1–5% molar excess, of tris(hydroxymethyl) aminomethane at a temperature between about 35 and about 60° C. for a period of from 1 to 5 hours to yield at least 99.9% pure bicyclic oxazolidine product and 2 moles of water by-product. The reaction medium is mixed until a clear solution is formed, insuring that all of the formaldehyde has reacted. The tris(hydroxymethyl)aminomethane co-reactant is added in portions throughout the reaction and continuously mixed to retain clarity in the production of the present product containing less than 0.1 wt. % free formaldehyde and other minor by-products.

The clear solution of the oxazolidine product, containing between about 1.0 and 60 wt. % glycols and between about 12 and about 15 wt. % water, is subsequently contacted at ambient or up to 50° C. elevated temperature with between about 0.1 and about 10 wt. %, preferably 0.1–5 wt. %, of IPBC which is added under agitation throughout a period of from about 1 to about 2.5 hours. The clear liquid composition thus produced exhibits broad spectrum biocidal properties effective against gram negative and gram positive bacteria as well as fungi which composition exhibits biocidal properties greater than the sum of those achievable with the individual components.

The liquid medium suitable for the condensation reaction and subsequent combination with IPBC is an aliphatic polyhydroxy compound such as a $C_3$ to $C_6$ diol or other liquid glycol, including propylene glycol, dipropylene glycol, tripropylene glycol, glycol triols, 1,4- and 1,3-dihydroxy butanes and ethoxylated and/or propoxylated derivatives phenoxy ethanol thereof or mixtures of these. Preferred of this group are polyethylene glycol-PEG 400, butanediol and phenoxyethanol.

The paraformaldehyde slurry introduced into the reactor is desirably a 45 to 75% glycol or phenoxy ethanol suspension which is continuously agitated during the reaction and gradually heated to reaction temperature. Since the paraformaldehyde and the tris(hydroxymethyl) aminomethane (THAM) are both of low solubility in the liquid medium, completion of the condensation reaction and depletion of the formaldehyde is indicated by the formation of a clear solution of soluble bicyclic oxazolidine.

The most preferred reaction conditions include maintaining the molar excess of the tris(hydroxymethyl)aminomethane between 1.1 and 3% until two moles of water by-product are formed and effecting the reaction over a period of from 3–4 hours at a temperature of 50–60° C.

The basic reaction forming the bicyclic hydroxymethyl oxazolidine is defined by the equation:

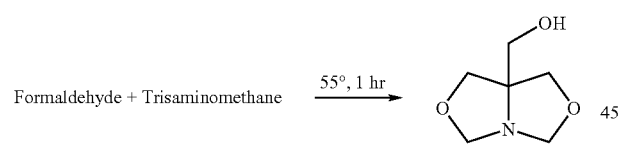

As pointed out above the present broad spectrum biocidal composition is particularly suitable for personal care formulations in a concentration of up to 5 wt. %, preferably 0.02–1.0% concentration, to prevent deterioration and extended shelf life of the product.

Also, the present composition is suitably employed in 0.02 to 1.0% concentrations to minimize degradation of industrial products such as paints, coatings, adhesives, sealants, caulks and the like. The following illustrate a few typical examples of suitable formulations to which the present preservative is beneficially added.

Some formulations which beneficially employ the product of this invention are presented in the following disclosure.

Having generally described the invention, reference is now had to the following examples which illustrate preferred embodiments but are not to be construed as limiting to the scope of the invention as set forth in the accompanying claims.

EXAMPLE 1

Preparation of Hydroxymethyl Oxazolidine/Iodopropynyl Butylcarbamate Biocidal Composition A closed vessel is charged with 102 g of 1,3-dihydroxybutane and 62 g of prilled paraformaldehyde is added and mixed at room temperature until a uniform slurry is formed. The slurry is then heated to 60° C. and a 2% molar (or 1–5%) molar excess of tris(hydroxymethyl)aminomethane (THAM) is introduced. A total of 124 g of 99% pure tris(hydroxymethyl)aminomethane is gradually added in increasing increments until a 2% molar excess is obtained. The ensuing condensation reaction takes place over a period of 3 hours. During the reaction, soluble bicyclic hydroxymethyl oxazolidine is continuously formed. Since paraformaldehyde and tris(hydroxymethyl)-aminomethane are of low solubility in the reaction medium, completion of the reaction is indicated when a clear solution is formed with water by-product. When the mixture becomes clear, insuring that all of the formaldehyde has reacted, the resulting solution is allowed to cool to ambient temperature and 4.42 g of powdered IPBC (weight ratio of bicyclic hydroxymethyl oxazolidine HMBO to IPBC is 33:1) is added and stirred until a clear solution is obtained. No crystallization of IPBC is noted in the substantially colorless product and a pure clear, liquid composition containing less than 1000 ppm of formaldehyde is obtained.

EXAMPLES 2–16

The above general procedure described in Example 1 was repeated in Examples 2–8, except that the weight ratio of HMBO to IPBC and reaction media were varied as noted in the following Table 1.

TABLE 1

| Ex. | Reaction media | Wt. ratio HMBO:IPBC | Description of Composition |
|---|---|---|---|
| 2 | propylene glycol | 17:1 | Clear |
| 3 | propylene glycol | 10:1 | Slight crystallization occurs |
| 4 | 1,3-butanediol | 100:1 | Clear |
| 5 | 1,3-butanediol | 33:1 | Clear |
| 6 | 1,3-butanediol | 17:1 | Clear |
| 7 | 1,3-butanediol | 10:1 | Clear |
| 8 | dipropylene glycol | 17:1 | Clear |
| 9 | dipropylene glycol | 10:1 | Clear |
| 10 | PEG-400 | 100:1 | Clear |
| 11 | PEG-400 | 33:1 | Clear |
| 12 | PEG-400 | 17:1 | Clear |
| 13 | PEG-400 | 10:1 | Clear |
| 14 | phenoxyethanol | 100:1 | Clear |
| 15 | phenoxyethanol | 33:1 | Clear |
| 16 | phenoxyethanol | 17:1 | Clear |

The present biocidal compositions Examples 1–3, 4, 8, 12, 13, 5, 6, 9, 10, 11 were evaluated for efficacy against:

A. *Candida albicans* 10231 yeast, (CAN)

B. *Staphylococcus aureus* 6538 bacteria, (SA)

C. *Pseudomonas aeruginosa* 9027, (PSA)

D. *Burkholderia cepacia* 25416, (BC)

E. *Escherichia coli* 8739 and (EC)

F. *Aspergillus niger* 16404 (mold) (AN)

employed in the following antimicrobial evaluations as reported in Table 2.

In the following tests, 1:2 molar ratio of tris(hydroxymethyl)-aminomethane to formaldehyde was used with 0.5% and 1.5% IPBC in emulsions I. or II. reported below.

| I. Standard Screening Emulsion | | II. Non-ionic Screening Emulsion | |
|---|---|---|---|
| Stearic acid | 5 wt. % | Water (distilled) | 70.1 wt. % |
| Mineral oil | 2.5 wt. % | Stabileze QM* | 0.20 wt. % |
| Cetyl alcohol | 1.0 wt. % | 2-ethyl hexylpalmitate | 10.0 wt. % |
| Ceteareth 5**** | 0.5 wt. % | Mix of cetyl & stearyl alcohols | 2.0 wt. % |
| Glyceryl Monostearate/ PEG 100Stearate | 1.5 wt. % | Ceteareth-20** | 2.0 wt. % |
| Water | 87.90 wt. % | Glyceryl stearate | 0.5 wt. % |
| Triethanolamine | 1.0 wt. % | Laureth-23*** | 2.50 wt. % |
| Citric acid, 30% aq. | 0.6 wt. % | Isocetylstearate | 10 wt. % |
| | | Triethanolamine | 0.2 wt. % |

*decadiene crosslinked methyl vinyl ether/Maleic anhydride copolymer
**mixture of $C_{16}$ & $C_{18}$ (ethoxy)20 alcohols
***polyoxyethylene(23) lauryl ether & mixture of $C_{16}$ & $C_{18}$ (ethoxy)5 alcohols
****polyethyleneglycol of cetearyl alcohol tic Soy Broth (TSB) for bacterial evaluations or to Malt Agar (M) for fungal evaluations. Antimicrobial activity was demonstrated against the bacterium *Bacillus subtilis* (ATCC 27328) or the fungi *Aureobasidium pullulans* (ATCC 9348) and *Aspergillus niger* (ATCC 6275). One hundred μl of the bacterial suspensions were added to TSB broth containing each biocide or biocide mixture to a final concentration of approximately $10^6$ CFU/ml. The inoculated broth was then incubated at 32° C. for 2–3 days. For fungi MIC, 10 μl of the fungi suspensions were pipetted to the solidified Malt agar containing various concentrations of each biocide or the biocide mixture. Final concentration about $10^5$ spores/ml. Plates were incubated for 10–12 days at 28° C.

The lowest concentration of each compound or mixture to inhibit visible growth at 32° C. after 2–3 days for bacteria and at 28° after 10–12 days for fungi were taken as the Minimal Inhibitory Concentration (MIC). The MIC was taken as endpoints of activity. End points for the mixture of HMBO and IPBC where then compared with the end points for the pure active compound when employed individually.

Synergism was determined by a commonly used method described by Kull, A. C., Eisman, P. C, Sylwestrowicz, H.,

TABLE 2

HMBO/1.5% or 3.0% IPBC in phenoxyethanol
SCREENING EMULSION

| Preservative | ppm acitves | Organism | 48 hrs | 7 days | 14 days | 21 days | 28 days |
|---|---|---|---|---|---|---|---|
| 49.3% HMBO/ 1.5% IPBC/ phenoxyethanol Use level - 0.1% | 493 ppm 15 ppm | SA | 70,000 | <10 | <10 | <10 | <10 |
| | | EC | 50 | <10 | <10 | <10 | <10 |
| | | PSA | <10 | <10 | <10 | <10 | <10 |
| | | BC | <10 | <10 | <10 | <10 | <10 |
| | | CAN | 4,000 | <10 | <10 | <10 | <10 |
| | | AN | <10 | <10 | <10 | <10 | <10 |
| 49.3% HMBO/ 1.5% IPBC/ phenoxyethanol use level - 0.2% | 986 ppm 30 ppm | SA | 34,000 | <10 | <10 | <10 | <10 |
| | | EC | 20 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| 48.5% HMBO/ 3.0% IPBC/ phenoxyethanol use level - 0.1% | 485 ppm 30 ppm | SA | 15,000 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| 48.5% HMBO/ 3.0% IPBC/ phenoxyethanol use level - 0.2% | 970 ppm 60 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| unpreserved | | SA | >1E6 | 390,000 | 4.50E+03 | 2.10E+02 | >1E4 |
| | | EC | >1E6 | 860 | >1E4 | >1E4 | >1E4 |
| | | PSA | >1E6 | 790 | >1E4 | >1E4 | >1E4 |
| | | BC | >1E6 | >1E6 | >1E4 | >1E4 | >1E4 |
| | | CAN | >1E6 | >1E6 | >1E6 | >1E6 | >1E6 |
| | | AN | >1E6 | >1E6 | >1E4 | >1E4 | >1E4 |

In repetitions of the above evaluations, there was significant reduction of the organisms after 48 hours for all solvent systems at a 0.2% emulsion dosage level.

EXAMPLE 17

MIC Data on Microbiological Media

To demonstrate synergism in microbiological growth media a wide range of concentrations and ratios of compounds, generated by serial dilutions were added into Tryp- D. and Mayer, R. L. (1961). *Applied Microbiology*, 9:538 using the ratio determined by: $Q_a/Q_A + Q_b/Q_B =$ Synergy Index (SI).

Wherein: QA is the concentration of HMBO in parts per million (ppm), acting alone, which produced and end point. Qa is the concentration of HMBO in ppm, in the mixture, which produced and end point. QB is the concentration of IPBC in ppm, acting alone, which produced an end point and Qb is the concentraton of IPBC in ppm, in the mixture, which produced an end point.

When the sum of Qa/QA+Qb/QB is greater than one, antagonism is indicated. When the sum is equal to one, additivity is indicated. When the sum is less than one, synergism is demonstrated.

The results, which serve to demonstrate the synergism of this biocidal combination in microbiological media are compiled in Table 3 as shown below, wherein compound A is HMBO containing less than 0.1 wt. % formaldehyde and compound B is IPBC.

TABLE 3

Low free formaldehyde HMBO (compound A)/
IPBC(compound B)

| Microorganism | A (ppm) | B (ppm) | A:B | Synergy Index |
|---|---|---|---|---|
| *Bacillus subtilis* | 250 | 0 | | |
| | 62.5 | 31.2 | 2:1 | 0.75 |
| | 0 | 62.5 | | |
| *Aspergillus niger* | 1,000 | 0 | | |
| | 50 | 0.1 | 500:1 | 0.45 |
| | 100 | 0.1 | 1,000:1 | 0.50 |
| | 500 | 0.1 | 5,000:1 | 0.90 |
| | 250 | 0.05 | 5,000:1 | 0.45 |
| | 500 | 0.05 | 10,000:1 | 0.70 |
| | 0 | 0.25 | | |
| *Alternaria alternata* | 250 | 0 | | |
| | 100 | 0.25 | 400:1 | 0.70 |
| | 250 | 0.10 | 2,500 | 0.70 |
| | 0 | 0.50 | | |

EXAMPLE 18

The efficacy of each individual compound or their combination was measured in a latex paint artificially contaminated with a mixed inoculum. The microbiological evaluations shown as examples, are based on ASTM D2574–94, "*Resistance of emulsion paints in the container to the attack of microorganisms*". Briefly, paint samples (e.g. Polyvinyl Acrylic, PCL 717) were prepared to contain different concentrations of each compound or their mixtures in different concentrations and ratios. Each paint sample thus prepared was then inoculated with a mixed culture of *Pseudomonas aeruginosa, Enterobacter cloacae, Bacillus subtilis, B. megaterium, B. licheniformis, Aspergillus niger* and *Penicillium funiculosum* (final concentration of about $10^6$ CFU/ml) and re-challenged after 7 days (final concentration of about $10^7$ CFU/ml). Paint samples were incubated at 32° C. for the duration of the test and sampled for the presence of viable bacteria on TSA and M plates. Growth was rated on a scale from "0" (no growth) to "4" (heavy growth). A paint sample was considered appropriately preserved if no bacterial growth ("0" rating) was detected after six days incubation in both challenge assays.

Table 4 shows the synergistic effects of the compounds when tested in a typical polyvinyl acrylic paint. The table summarizes the results obtained when mixtures of the low formaldehyde hydroxymethyl oxazolidine (HMBO) (compound A) and IPBC (compound B) in PEG-400 were tested.

TABLE 4

| Ratio Actives (A:B) | Total Actives PPM | TSA plates CI | | | | TSA plates CII | | | | MALT Plates CI | | | | MALT Plates CII | | | |
|---|---|---|---|---|---|---|---|---|---|---|---|---|---|---|---|---|---|
| | | 1 | 2 | 3 | 6 | 1 | 2 | 3 | 6 | 1 | 2 | 3 | 6 | 1 | 2 | 3 | 6 |
| 25:1 | 380 (365:15) | 1 | 0 | 0 | 0 | 1 | 0 | 0 | 0 | 1 | 0 | 0 | 0 | 0 | 0 | 1 | 0 |
| 17:1 | 545 (515:30) | 0 | 0 | 1 | 0 | 1 | 1 | 0 | 0 | 0 | 0 | 0 | 0 | 1 | 1 | 0 | 0 |
| A alone | 500 | 0 | 0 | 0 | 0 | 1 | 1 | 1 | 1 | 0 | 0 | 0 | 0 | 0 | 0 | 0 | 0 |
| | 520 | 0 | 0 | 0 | 0 | 0 | 0 | 1 | 0 | 0 | 0 | 0 | 0 | 0 | 1 | 1 | 0 |
| B alone | 60 | 0 | 0 | 1 | 0 | 4 | 4 | 4 | 3 | 0 | 1 | 0 | 0 | 4 | 4 | 4 | 4 |
| | 120 | 4 | 2 | 0 | 0 | 4 | 3 | 3 | 3 | 4 | 4 | 2 | 0 | 4 | 4 | 4 | 4 |
| | 200 | 4 | 2 | 0 | 0 | 4 | 3 | 3 | 3 | 4 | 2 | 1 | 0 | 4 | 4 | 4 | 4 |
| Control | — | 1 | 0 | 0 | 0 | 4 | 4 | 4 | 3 | 0 | 1 | 0 | 0 | 4 | 4 | 4 | 4 |

The present low formaldehyde HMBO/IPBC emulsion was tested with various organisms in different solvents. The results of these tests is reported in following Tables 5–11.

TABLE 5

48.5% HMBO/3% IPBC in different solvent systems
SCREENING EMULSION

| Preservative | ppm active | Organism | 48 hrs | 7 days | 14 days | 21 days | 28 days |
|---|---|---|---|---|---|---|---|
| HMBO/3% IPBC in propylene glycol 0.1% use level | 485 HMBO 30 IPBC | SA | 270 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| HMBO/3% IPBC dipropylene glycol | 485 HMBO 30 IPBC | SA | 70 | <10 | <10 | <10 | <10 |
| | | EC | <10 | <10 | <10 | <10 | <10 |
| | | PSA | <10 | <10 | <10 | <10 | <10 |

TABLE 5-continued 48.5% HMBO/3% IPBC in different solvent systems
SCREENING EMULSION

| Preservative | ppm active | Organism | 48 hrs | 7 days | 14 days | 21 days | 28 days |
|---|---|---|---|---|---|---|---|
| 0.1% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/3% IPBC | 485 HMBO | SA | 20 | <10 | <10 | <10 | <10 |
| polyethylene | 30 IPBC | EC | <10 | <10 | <10 | <10 | <10 |
| glycol | | PSA | <10 | <10 | <10 | <10 | <10 |
| 0.1% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/3% IPBC | 485 HMBO | SA | <10 | <10 | <10 | <10 | <10 |
| 1,3 butanediol | 30 IPBC | EC | <10 | <10 | <10 | <10 | <10 |
| 0.1% use level | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| unpreserved | | SA | >1E6 | 17,000 | 70 | 60 | >1E4 |
| | | EC | 61,000 | 249,000 | >1E4 | >1E4 | >1E4 |
| | | PSA | 8,000 | 1.00E+04 | >1E4 | >1E4 | >1E4 |
| | | BC | >1E6 | >1E6 | >1E4 | >1E4 | >1E4 |
| | | CAN | 600,000 | 580,000 | >1E4 | >1E4 | >1E4 |
| | | AN | 75,000 | 140,000 | >1E4 | >1E4 | >1E4 |

TABLE 6

47.5% HMBO/5% IPBC in different solvent systems
SCREENING EMULSION

| Preservative | ppm actives | Organism | 48 hrs | 7 days | 14 days | 21 days | 28 days |
|---|---|---|---|---|---|---|---|
| HMBO/5% IPBC | 475 HMBO | SA | 240 | <10 | <10 | <10 | <10 |
| in propylene | 50 IPBC | EC | <10 | <10 | <10 | <10 | <10 |
| glycol | | PSA | <10 | <10 | <10 | <10 | <10 |
| 0.1% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/5% IPBC | 475 HMBO | SA | 100 | <10 | <10 | <10 | <10 |
| dipropylene | 50 IPBC | EC | <10 | <10 | <10 | <10 | <10 |
| glycol | | PSA | <10 | <10 | <10 | <10 | <10 |
| 0.1% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/5% IPBC | 475 HMBO | SA | <10 | <10 | <10 | <10 | <10 |
| polyethylene | 50 IPBC | EC | <10 | <10 | <10 | <10 | <10 |
| glycol | | PSA | <10 | <10 | <10 | <10 | <10 |
| 0.1% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/5% IPBC | 475 HMBO | SA | <10 | <10 | <10 | <10 | <10 |
| 1,3 butanediol | 50 IPBC | EC | <10 | <10 | <10 | <10 | <10 |
| 0.1% use level | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| unpreserved | | SA | >1E6 | 17,000 | 70 | 60 | >1E4 |
| | | EC | 61,000 | 249,000 | >1E4 | >1E4 | >1E4 |
| | | PSA | 8,000 | 1.00E+04 | >1E4 | >1E4 | >1E4 |
| | | BC | >1E6 | >1E6 | >1E4 | >1E4 | >1E4 |
| | | CAN | 600,000 | 580,000 | >1E4 | >1E4 | >1E4 |
| | | AN | 75,000 | 140,000 | >1E4 | >1E4 | >1E4 |

TABLE 7

48.5% HMBO/3% IPBC in different solvent systems
SCREENING EMULSION

| Preservative | Use Level | Organism | 48 hrs | 7 days | 14 days | 21 days | 28 days |
|---|---|---|---|---|---|---|---|
| HMBO/3% IPBC | 1940 HMBO | SA | <10 | <10 | <10 | <10 | <10 |
| in propylene | 120 IPBC | EC | <10 | <10 | <10 | <10 | <10 |

TABLE 7-continued

48.5% HMBO/3% IPBC in different solvent systems
SCREENING EMULSION

| Preservative | Use Level | Organism | 48 hrs | 7 days | 14 days | 21 days | 28 days |
|---|---|---|---|---|---|---|---|
| glycol | | PSA | <10 | <10 | <10 | <10 | <10 |
| 0.4% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/3% IPBC | 1940 HMBO | SA | <10 | <10 | <10 | <10 | <10 |
| dipropylene | 120 IPBC | EC | <10 | <10 | <10 | <10 | <10 |
| glycol | | PSA | <10 | <10 | <10 | <10 | <10 |
| 0.4% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/3% IPBC | 1940 HMBO | SA | <10 | <10 | <10 | <10 | <10 |
| polyethylene | 120 IPBC | EC | <10 | <10 | <10 | <10 | <10 |
| glycol | | PSA | <10 | <10 | <10 | <10 | <10 |
| 0.4% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/3% IPBC | 1940 HMBO | SA | <10 | <10 | <10 | <10 | <10 |
| 1,3 butanediol | 120 IPBC | EC | <10 | <10 | <10 | <10 | <10 |
| 0.4% use level | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| unpreserved | | SA | >1E6 | 17,000 | 7.00E+01 | 6.00E+01 | >1E4 |
| | | EC | 61,000 | 249,000 | >1E4 | >1E4 | >1E4 |
| | | PSA | 8,000 | 10,000 | >1E4 | >1E4 | >1E4 |
| | | BC | >1E6 | >1E6 | >1E4 | >1E4 | >1E4 |
| | | CAN | 600,000 | 5.80E+05 | >1E4 | >1E4 | >1E4 |
| | | AN | 75,000 | 140,000 | >1E4 | >1E4 | >1E4 |

TABLE 8

47.5% HMBO/5% IPBC in different solvent systems
SCREENING EMULSION

| Preservative | ppm actives | Organism | 48 hrs | 7 days | 14 days | 21 days | 28 days |
|---|---|---|---|---|---|---|---|
| HMBO/5% IPBC | 1900 HMBO | SA | <10 | <10 | <10 | <10 | <10 |
| in propylene | 200 IPBC | EC | <10 | <10 | <10 | <10 | <10 |
| glycol | | PSA | <10 | <10 | <10 | <10 | <10 |
| 0.4% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/5% IPBC | 1900 HMBO | SA | <10 | <10 | <10 | <10 | <10 |
| dipropylene | 200 IPBC | EC | <10 | <10 | <10 | <10 | <10 |
| glycol | | PSA | <10 | <10 | <10 | <10 | <10 |
| 0.4% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/5% IPBC | 1900 HMBO | SA | <10 | <10 | <10 | <10 | <10 |
| polyethylene | 200 IPBC | EC | <10 | <10 | <10 | <10 | <10 |
| glycol | | PSA | <10 | <10 | <10 | <10 | <10 |
| 0.4% use level | | BC | <10 | <10 | <10 | <10 | <10 |
| | | CAN | <10 | <10 | <10 | <10 | <10 |
| | | AN | <10 | <10 | <10 | <10 | <10 |
| HMBO/5% IPBC | 1900 HMBO | SA | <10 | <10 | <10 | <10 | <10 |
| 1,3 butanediol | 200 IPBC | EC | <10 | <10 | <10 | <10 | <10 |
| 0.4% use level | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| unpreserved | | SA | >1E6 | 17,000 | 7.00E+01 | 6.00E+01 | >1E4 |
| | | EC | 61,000 | 249,000 | >1E4 | >1E4 | >1E4 |
| | | PSA | 8,000 | 10,000 | >1E4 | >1E4 | >1E4 |
| | | BC | >1E6 | >1E6 | >1E4 | >1E4 | >1E4 |
| | | CAN | 600,000 | 5.80E+05 | >1E4 | >1E4 | >1E4 |
| | | AN | 75,000 | 140,000 | >1E4 | >1E4 | >1E4 |

TABLE 9

48.5% HMBO/3% IPBC in different solvent systems
NONIONIC EMULSION BASE

| Preservative | ppm actives | Organism | 48 hrs | 7 days | 14 days | 21 days | 28 days |
|---|---|---|---|---|---|---|---|
| HMBO/3% IPBC in propylene glycol 0.2% use level | 970 HMBO 60 IPBC | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 20,000 | <10 | <10 | <10 | <10 |
| | | AN | <10 | <10 | <10 | <10 | <10 |
| HMBO/3% IPBC dipropylene glycol 0.2% use level | 970 HMBO 60 IPBC | SA | <10 | <10 | <10 | <10 | <10 |
| | | EC | 6.60E+02 | <10 | <10 | <10 | <10 |
| | | PSA | <10 | <10 | <10 | <10 | <10 |
| | | BC | <10 | <10 | <10 | <10 | <10 |
| | | CAN | 33,000 | <10 | <10 | <10 | <10 |
| | | AN | <10 | <10 | <10 | <10 | <10 |
| HMBO/3% IPBC polyethylene glycol 0.2% use level | 970 HMBO 60 IPBC | SA | <10 | <10 | <10 | <10 | <10 |
| | | EC | 90 | <10 | <10 | <10 | <10 |
| | | PSA | <10 | <10 | <10 | <10 | <10 |
| | | BC | <10 | <10 | <10 | <10 | <10 |
| | | CAN | 13,000 | <10 | <10 | <10 | <10 |
| | | AN | <10 | <10 | <10 | <10 | <10 |
| HMBO/3% IPBC 1,3 butanediol 0.2% use level | 970 HMBO 60 IPBC | SA | 10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 30,000 | <10 | <10 | <10 | <10 |
| | | AN | <10 | <10 | <10 | <10 | <10 |
| unpreserved | | SA | >1E6 | >1E4 | 7.60E+03 | 4.00E+01 | >1E4 |
| | | EC | >1E6 | >1E4 | >1E4 | >1E4 | >1E4 |
| | | PSA | >1E6 | >1E4 | >1E4 | >1E4 | >1E4 |
| | | BC | >1E6 | >1E4 | >1E4 | >1E4 | >1E4 |
| | | CAN | >1E6 | >1E4 | >1E4 | >1E4 | >1E4 |
| | | AN | 320,000 | >1E4 | >1E4 | >1E4 | >1E4 |

TABLE 10

48.5% HMBO/3% IPBC in different solvent systems
NONIONIC EMULSION

| Preservative | ppm actives | Organism | 48 hrs | 7 days | 14 days | 21 days | 28 days |
|---|---|---|---|---|---|---|---|
| HMBO/3% IPBC in propylene glycol 0.4% use level | 1940 HMBO 120 IPBC | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 900 | <10 | <10 | <10 | <10 |
| | | AN | <10 | <10 | <10 | <10 | <10 |
| HMBO/3% IPBC dipropylene glycol 0.4% use level | 1940 HMBO 120 IPBC | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 3,000 | <10 | <10 | <10 | <10 |
| | | AN | <10 | <10 | <10 | <10 | <10 |
| HMBO/3% IPBC polyethylene glycol 0.4% use level | 1940 HMBO 120 IPBC | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 2,000 | <10 | <10 | <10 | <10 |
| | | AN | <10 | <10 | <10 | <10 | <10 |
| HMBO/3% IPBC 1,3 butanediol 0.4% use level | 1940 HMBO 120 IPBC | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 960 | <10 | <10 | <10 | <10 |
| | | AN | <10 | <10 | <10 | <10 | <10 |
| unpreserved | | SA | >1E6 | >1E4 | 7.60E+03 | 4.00E+01 | >1E4 |
| | | EC | >1E6 | >1E4 | >1E4 | >1E4 | >1E4 |
| | | PSA | >1E6 | >1E4 | >1E4 | >1E4 | >1E4 |
| | | BC | >1E6 | >1E4 | >1E4 | >1E4 | >1E4 |
| | | CAN | >1E6 | >1E4 | >1E4 | >1E4 | >1E4 |
| | | AN | 320,000 | >1E4 | >1E4 | >1E4 | >1E4 |

TABLE 11

| | | | 49.3% HMBO/1.5% IPBC in 1,3 butanediol SCREENING EMULSION | | | | |
|---|---|---|---|---|---|---|---|
| Preservative | ppm acitves | Organism | 48 hrs | 7 days | 14 days | 21 days | 28 days |
| HMBO/1.5% IPBC | 986 HMBO | SA | 410 | <10 | <10 | <10 | <10 |
| 1,3 butanediol | 30 IPBC | EC | <10 | <10 | <10 | <10 | <10 |
| 0.2% use level | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| HMBO/1.5% O{BC | 493 HMBO | SA | 9,000 | <10 | <10 | <10 | <10 |
| 1,3 butanediol | 15 IPBC | EC | <10 | <10 | <10 | <10 | <10 |
| 0.1% use level | | PSA | <10 | <10 | <10 | <10 | <10 |
| | | BC | <10 | <10 | <10 | <10 | <10 |
| | | CAN | 460 | <10 | <10 | <10 | <10 |
| | | AN | 20 | <10 | <10 | <10 | <10 |
| HMBO/1.5% IPBC | 247 HMBO | SA | 4,100,000 | <10 | <10 | <10 | <10 |
| 1,3 butanediol | 7.5 IPBC | EC | 1,000 | <10 | <10 | <10 | <10 |
| .05% use level | | PSA | <10 | <10 | <10 | <10 | <10 |
| | | BC | <10 | <10 | <10 | <10 | <10 |
| | | CAN | 170,000 | <10 | <10 | <10 | <10 |
| | | AN | 50 | <10 | <10 | <10 | <10 |
| unpreserved | | SA | >1E6 | >1E4 | >1E4 | >1E4 | >1E4 |
| | | EC | 600,000 | >1E4 | >1E4 | >1E4 | >1E4 |
| | | PSA | >1E6 | >1E4 | >1E4 | >1E4 | >1E4 |
| | | BC | >1E6 | >1E4 | >1E4 | >1E4 | >1E4 |
| | | CAN | >1E6 | 360,000 | >1E4 | >1E4 | >1E4 |
| | | AN | >1E6 | 220,000 | >1E4 | >1E4 | >1E4 |

What is claimed is:

1. A broad spectrum, synergistic biocidal composition comprising a mixture of a biocidal cyclic hydroxymethyl oxazolidine having the formula

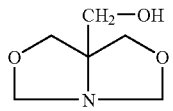

containing less than 0.1 wt. % free formaldehyde and between about 0.1 and about 10 wt. % of iodopropynyl butylcarbamate in an aqueous solution of a polyhydroxide of a $C_3$ to $C_6$ aliphatic hydrocarbon, a phenoxyethanol or a mixture thereof.

2. The composition of claim 1 wherein the composition contains between 0.1 and 5 wt. % of iodopropynyl butylcarbamate.

3. The composition of claim 1 wherein the weight ratio of hydroxymethyl oxazolidine to iodopropynyl butyl carbamate is between about 10:1 and about 100:1.

4. A personal care formulation containing a biocidal amount between 0.05 and 1.0 wt. % of the composition of claim 1.

5. The personal care formulation of claim 4 selected from the group consisting of a hair spray, hair dye, skin lotion and hair conditioner.

6. An industrial formulation selected from the group of a paint, adhesive, ink, pigment dispersion or slurry, paper pulp mixture, latex emulsion, metalworking fluid, caulk and sealant containing between about 0.05–1.0 wt. % of the composition of claim 1.

7. A broad spectrum, synergistic biocidal composition comprising a mixture of a biocidal cyclic hydroxymethyl oxazolidine having the formula

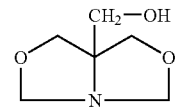

containing less than 0.1 wt. % free formaldehyde and between 0.1 and about 10 wt. % of iodopropynyl butylcarbamate in an aqueous solution of a compound selected from the group consisting of a $C_3$ to $C_6$ diol, phenoxyethanol optionally alkoxylated with a $C_2$ to $C_3$ alkoxyl group, polyethylene glycol and mixtures thereof.

8. The composition of claim 7 wherein said solution is an aqueous solution of butanediol, phenoxyethanol or a mixture thereof.

9. A personal care formulation containing 0.05 to 1.0 wt. % biocidal amount of the composition of claim 7.

10. A process which comprises:
   (a) forming a uniform slurry of paraformaldehyde in a liquid selected from the group consisting of an aqueous solution of a polyhydroxide of a $C_3$ to $C_6$ hydrocarbon, phenoxyethanol, ethoxylated or propoxylated phenoxyethanol, polyethylene glycol, polypropylene glycol or a mixture thereof;
   (b) heating the slurry to a temperature of from about 35 to about 60° C.;
   (c) introducing a 0.75 to 5 molar excess of tris(hydroxymethyl)-aminomethane into said slurry;
   (d) agitating the mixture of (c) while constantly maintaining said excess of tris(hydoroxymethyl)aminomethane until completion of the reaction indicated by the formation of the substantially pure cyclic hydroxymethyl oxazolidine in a clear solution;

(e) adding between about 0.1 and about 10 wt. % of iodopropynyl butylcarbamate, based on said oxazolidine, to the product of step (d);

(f) constantly agitating the contents of (e) until a second clear solution is formed and recovering the solution of (f) as a solution of composition containing less than 0.1 wt. % free formaldehyde, iodopropynyl butylcarbamate and cyclic hydroxymethyl oxazolidione having the formula

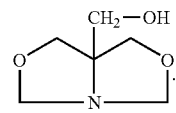

11. The process of claim 10 wherein said aqueous solution in step (a) is butanediol or phenoxyethanol or a mixture thereof.

* * * * *